United States Patent [19]
Shirafuji et al.

[11] Patent Number: 4,716,253
[45] Date of Patent: Dec. 29, 1987

[54] METHOD FOR PRODUCING CYCLOALKANOLS

[75] Inventors: Tamio Shirafuji; Kiyomi Sakai, both of Niihama; Ken-ichi Hirose, Settsu, all of Japan

[73] Assignee: Sumitomo Chemical Company, Limited, Osaka, Japan

[21] Appl. No.: 929,510

[22] Filed: Nov. 12, 1986

[30] Foreign Application Priority Data

Nov. 19, 1985 [JP] Japan ................. 60-259479
Nov. 25, 1985 [JP] Japan ................. 60-265904

[51] Int. Cl.$^4$ ................. C07C 29/04; C07C 35/18
[52] U.S. Cl. ................. 568/895; 568/835
[58] Field of Search ............ 568/821, 822, 835, 838, 568/895

[56] References Cited

U.S. PATENT DOCUMENTS

| 4,469,905 | 9/1984 | Inwood et al. ............ 568/835 |
| 4,499,313 | 2/1985 | Okumura et al. .......... 568/835 |
| 4,507,512 | 3/1985 | Okumura et al. .......... 568/835 |
| 4,528,409 | 7/1985 | Mitsui et al. ............. 568/835 |
| 4,595,786 | 7/1986 | Waller .................... 568/822 |

FOREIGN PATENT DOCUMENTS

| 686257 | 5/1964 | Canada ................... 568/835 |
| 123713 | 11/1984 | European Pat. Off. ...... 568/835 |
| 124723 | 1/1983 | Japan .................... 568/838 |
| 194828 | 11/1983 | Japan .................... 568/838 |
| 104029 | 6/1985 | Japan .................... 568/835 |
| 1015852 | 1/1986 | Japan .................... 568/835 |
| 918406 | 2/1963 | United Kingdom .......... 568/835 |

OTHER PUBLICATIONS

Chemical Abstracts, 72, 12209z (Abstract of Japanese Pat. Publn., No 26656/1969).
Chemical Abstracts, 78, 57738m (Abstract of Japanese Pat. Publn. No. 45323/1972).
Chemical Abstracts, 102, 148714f (Abstract of Japanese Pat. Appln. Laid-open Nos. 222431 & 222432/1984).
Chemical Abstracts, 104, 50589k (Abstract of Japanese Pat. Appln. Laid-open No. 104028/1985).
Chemical Abstracts, 103, 123068f (Abstract of Japanese Pat. Appln. Laid-Open No. 104029/1985).
Chemical Abstracts, 103, 123066d (Abstract of Japanese Pat. Appln. Laid-Open No. 104030/1985).
Chemical Abstracts, 103, 123067e (Abstract of Japanese Pat. Appln. Laid-open No. 104031/1985).

Primary Examiner—Werren B. Lone
Attorney, Agent, or Firm—Stevens, Davis, Miller & Mosher

[57] ABSTRACT

A method for producing a cycloalkanol important as a material for caprolactam, adipic acid and the like by the hydration of a cycloalkene with a solid acid as a catalyst, which comprises carrying out said hydration in the presence of a phenol.

11 Claims, No Drawings

METHOD FOR PRODUCING CYCLOALKANOLS

The present invention relates to a method for producing cycloalkanols which are important as a material for caprolactam, adipic acid, etc., and more particularly, to industrially excellent improvements in a method of producing cycloalkanols by hydrating cycloalkenes with solid acids as a catalyst.

A method of producing cycloalkanols by hydrating cycloalkenes with solid acids as a catalyst is already well known.

Japanese Patent Publication No. 15619/1963 discloses a method of producing cyclohexanol by hydrating cyclohexene in the presence of an emulsifier using a strongly acidic cation exchanger. According to the description in the specification of the patent, from 28.1 to 31.0 parts by weight of cyclohexanol is obtained from 200 parts by weight of cyclohexene. Upon calculation based on this description, the yield of cyclohexanol based on cyclohexene is from 11.5 to 12.7%.

Japanese Patent Publication No. 26656/1969 discloses a method of producing cyclohexanol by hydrating cyclohexene in the presence of a strong acid using a strongly acidic cation exchange resin. According to the description in the specification of the patent, the conversion of cyclohexene to cyclohexanol is from 12.6 to 14.4%.

Japanese Patent Publication No. 45323/1972 discloses a method of producing alcohols by hydrating olefins with dealkalized mordenite, clinoptilolite or faujasite series zeolite as a catalyst. The specification of this patent describes that: In the hydration of ethylene, the conversion of fed water to ethyl alcohol is from 0.4 to 8.1%, and upon calculation based thereon, the conversion of ethylene to ethyl alcohol is from 0.1 to 1.6%; in the hydration of propylene, the conversion of fed water to isopropyl alcohol is from 0.1 to 5.9%, and upon calculation based thereon, the conversion of propylene to isopropyl alcohol is from 0.1 to 20.7%; in the hydration of 1-butene, the conversion of fed water to sec-butyl alcohol is from 0.1 to 1.5%, and upon calculation based thereon, the conversion of 1-butene to sec-butyl alcohol is from 0.1 to 7.0%; and further, in the hydration of cyclohexene, the conversion of fed water to cyclohexanol is from 0.05 to 0.06%, and upon calculation based thereon, the conversion of cyclohexene to cyclohexanol is from 0.07 to 0.08%.

Japanese Patent Application Kokai (Laid-open) No. 194828/1983 disclosed a method of producing cycloalkanols by the catalytic hydration of cycloalkenes in the presence or absence of an organic solvent using as a catalyst crystalline aluminosilicate in which the molar ratio of silica to alumina is 20 or more. The specification of this patent describes that: In the hydration of cyclohexene with ZSM series zeolite developed by Mobil Oil Co., for example ZSM-5 (silica:alumina molar ratio, 60 and 25) and ZSM-12 (silica:alumina molar ratio, 70), as a catalyst, the yield of cyclohexanol is from 9 to 15%; and when an organic solvent such as tetrabromoethane, ethanol, isopropanol and ethylene glycol dimethyl ether is added in the above catalytic hydration at a rate of 50 g/10 g of cyclohexene, the yield of cyclohexanol is from 25 to 32%.

Japanese Patent Application Kokai (Laid-open) No. 222431/1984 discloses a method of producing alcohol by the hydration of olefins in the presence of H-mordenite or H-zeolite Y of a silica:alumina molar ratio of 20 to 500. The specification of this patent describes that: In the hydration of 1-butene, the yield of sec-butanol is from 1.0 to 11.5%. Also, in the hydration of other olefins by this method, the yield of the corresponding alcohols is as follows: Ethanol, 6.8%; isopropanol, 18%; sec-butanol, 10%; 2-pentanol, 6.5%; 2-hexanol, 5.6%; and cyclohexanol, 5.1%.

Japanese Patent Application Kokai (Laid-open) No. 222432/1984 discloses a method of producing alcohols by the hydration of olefins in the presence of a sulfone and H-mordenite or H-zeolite Y of a silica:alumina molar ratio of 20 to 500. The specification of this patent describes that: In the hydration of 1-butene in the presence of dimethyl sulfone, the yield of sec-butanol is 16.1%. Also, in the hydration of other olefins by this method, the yield of the corresponding alcohols is as follows: Ethanol, 6.7%; isopropanol, 12.4%; sec-butanol, 13.3%; 2-pentanol, 8.8%; 2-hexanol, 7.5%; and cyclohexanol, 8.2%.

Japanese Patent Application Kokai (Laid-open) No. 104028/1985 discloses a method of producing cyclic alcohols by the catalytic hydration of cyclic olefins in a liquid phase using crystalline aluminosilicate in which the proportion of acid sites on its outer surface to the whole acid sites is 0.07 or more. The specification of this patent dscribes that, in the hydration of cyclohexene, the cyclohexanol concentration of the oily phase after reaction is from 3.5 to 22.8 wt. %. There is no description about the yield of cyclohexanol, but Example 4 describes that the cyclohexanol concentration of the oily phase is 22 wt. % and that of the aqueous phase is 2% with other products than cyclohexanol being not detected. Upon calculation based on the assumption that the oily phase consists of cyclohexanol and cyclohexene and the aqueous phase consists of cyclohexanol and water, the yield of cyclohexanol is 21.4%.

Japanese Patent Application Kokai (Laid-open) No. 104029/1985 discloses a method of producing cyclic alcohols by the catalytic hydration of cyclic olefins using as a catalyst mordenite, faujasite or ferrierite series zeolite, all of which have a silica:alumina molar ratio of at least 20. The specification of this patent describes that the yield of cyclohexanol is from 8.5 to 14.2%.

Japanese Patent Application Kokai (Laid-open) No. 104030/1985 discloses a method of producing cycloalkanols by the hydration of cycloolefins using as a catalyst crystalline aluminosilicate having a composition corresponding to $M_2O \cdot Al_2O_3 \cdot XSiO_2$ (in which M represents at least one member selected from the group consisting of alkali metal ions, an ammonium ion and a hydrogen ion, and X represents a number of from 10 to 1000) characterized by the particular diffraction angle ($2\theta$) and relative strength in the X-ray diffraction pattern, in which a part or all of the alkali metal ions and/or ammonium ion have been substituted with a hydrogen ion. The specification of this patent describes that the conversion of cyclohexene is from 6.8 to 12.3% and the selectivity of cyclohexanol is from 90 to 100%. Upon calculation based thereon, the yield of cyclohexanol is from 6.1 to 12.3%.

Japanese Patent Application Kokai (Laid-open) No. 104031/1985 discloses a method of producing cyclic alcohols by the catalytic hydration of cyclic olefins with zeolite treated as follows as a catalyst: Some of aluminum atoms are expelled from their sites in the skeleton of zeolite crystals, and the empty sites are filled with silicon atoms from external sources so that the number of the empty sites is reduced to make the silica:alumina molar ratio at least 20. The specification of this patent describes that the yield of cyclohexanol is from 7.8 to 12.7%.

Further, Japanese Patent Application Kokai (Laid-open) No. 115542/1985 discloses a method of producing cyclopentanol from cyclopentene in the presence of an alcohol such as tetrahydrofurfuryl alcohol, etc. using a strongly acidic ion-exchange resin. The specification of this patent describes that a maximum yield of cyclopentanol is 19.7%.

In the methods to produce cycloalkanols by the hydration of cycloalkenes, the unreacted cycloalkene and water should be removed from the reaction mixture after reaction in order to recover the formed cycloalkanol. The removal of the cycloalkene and water requires large quantities of heat and costs much, because it is attained by distillation, etc. Because of this, it is preferred that the unreacted cycloalkene and water are little, in other words, the yield of cycloalkanol is high.

The conventional methods, however, are not satisfactory from industrial viewpoint, because their yield is very low.

An object of the present invention is to increase the yield, thereby finding an industrially advantageous method.

In view of the situation like this, the present inventors extensively studied a method for producing cycloalkanols in high yields by the hydration of cycloalkenes, and as a result, found that the yield of cycloalkanols can be increased by carrying out the hydration in the presence of a phenol. The present inventors thus completed the present invention.

The present invention provides a method for producing cycloalkanols by the hydration of cycloalkenes with solid acids as a catalyst characterized in that said hydration is carried out in the presence of a phenol.

In the method of the present invention, the solid acid used as a catalyst may be any of those belonging to mineral acids, metal salts, ion exchangers and metal oxides. Specifically, those belonging to mineral acids include phosphoric acids, heteropoly-acid or their salts supported on carriers (e.g. diatomaceous earth, silica gel, alumina, activated carbon), silicophosphoric acid, etc. Those belonging to metal salts include sulfates of Fe, Al, Cr, Co and Cu, the sulfates supported on silica, phosphates of B, Al, Cr, Zr, Fe and Mn, etc. Those belonging to ion exchangers include sulfonic acid type cation-exchange resins, acid-treated or ion-exchanged montmorillonite, etc. Those belonging to metal oxides include tungsten oxides ($WO_3$, $W_2O_5$), mixtures of the tungsten oxides with ZnO or $Cr_2O_3$, $Al(OH)_3$, $SiO_2 \cdot Al_2O_3$, zirconium tungstate, $MoO_3$-$ZrO_2$, $TiO_2$-$SiO_2$, $TiO_2$-ZnO, $NbO_3 \cdot nH_2O$, etc. [Reference cited: Catalyst Course Vol.8 (Industrial Catalytic Reaction, 2nd volume), Industrial Catalytic Reaction I, pp. 295, edited by Shokubai Gakkai, published by Kodansha, Tokyo, 1985]. Other specific examples include various kinds of zeolite such as mordenite, clinoptilolite, faujasite, ferrierite, ZSM, AZ-1 [Japanese Patent Application Kokai (Laid-open) No. 128210/1984], TPZ-3 (ibid., No. 110419/1983), Nu-3 (ibid., No. 3714/1982), Nu-5 (ibid., No. 129820/1982), Nu-6 (ibid., No. 123817/1982), Nu-10 (ibid., No. 200218/1982), etc.

In the method of the present invention, cycloalkenes used as a material are preferably those having from 5 to 8 carbon atoms. For example, there may be mentioned cyclopentene, cyclohexene, cyclooctene, 1,5-cyclooctadiene, etc.

Phenols used in the method of the present invention are phenol and substituted phenols, being compounds having one or more hydroxyl groups directly bonded to a benzene ring.

Specific examples of the phenols are compounds represented by the formula,

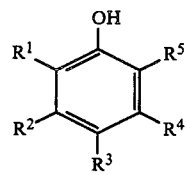

wherein $R^1$, $R^2$, $R^3$, $R^4$ and $R^5$ independently represent hydrogen, lower alkyl, phenyl, substituted phenyl, halogen, hydroxyl, lower alkoxyl, lower alkoxycarbonyl, carboxyl, nitro, mercapto, lower alkylthio or sulfonic. Also, the phenols may be compounds in which optional two adjacent groups among $R^1$ to $R^5$, taken together, form a benzene ring together with the carbon atoms of benzene to which the adjacent groups are bonded, respectively.

Examples of the phenols include phenol, cresol, xylenol, trimethylphenol, ethylphenol, isopropylphenol, tert-butylphenol, phenylphenol, tolylphenol, cyanophenol, chlorophenol, bromophenol, iodophenol, pyrocatechol, resorcinol, hydroquinone, pyrogallol, hydroquinone monomethyl ether, methyl salicylate, salicylic acid, 4-hydroxybenzoic acid, nitrophenol, mercaptophenol, methylthiophenol, phenolsulfonic acid, naphthol, sulfosalicylic acid, etc.

The amount of the phenol is from about 0.01 to about 10 moles based on 1 mole of cycloalkenes.

In the method of the present invention, the amount of water is generally from about 1 to about 100 moles based on 1 mole of cycloalkenes.

In the method of the present invention, the reaction temperature is from about 50° to about 200° C., preferably from 70° to 150° C. Reaction temperatures lower than 50° C. retard the reaction rate, being not practical. While, reaction temperatures higher than 200° C. shift the position of chemical equilibrium toward the cycloalkene side, being disadvantageous.

In the method of the present invention, a preferred reaction pressure is one which is higher than that required to cause the cycloalkene to retain a liquid phase under given reaction conditions. However, pressures under which the olefin is sufficiently dissolved in the reaction solution will do. The pressure may be controlled by means of inert gases such as a nitrogen gas.

In the method of the present invention, the reaction form may be any of a batchwise and continuous forms. Also, in the continuous form, any of forms with a fixbed reactor and tank-flow reactor may be employed.

According to the present invention, a method of producing cycloa,lkanols by the hydration of cycloalkenes with solid acids as a catalyst gives markedly improved yields as compared with the conventional methods by carrying out said hydration in the presence of a phenol.

The method of the present invention will be illustrated more specifically with reference to the following examples, but it is not limited to these examples. The yield of cycloalkanols used in the explanation is a value calculated by means of the following equation:

$$\text{Yield (\%)} = \frac{\text{Number of moles of formed cycloalkanol}}{\text{Number of moles of fed cycloalkene}} \times 100$$

REFERENCE EXAMPLE 1

Stock solutions of the following compositions were first prepared.

| A solution: | |
|---|---|
| Water | 433 g |
| $H_2SO_4$ | 44.8 g |
| $Al_2(SO_4)_3 \cdot 16-18H_2O$ | 15.5 g |
| $(n-Pr)_4NBr$ | 54.3 g |
| B solution: | |
| Water | 320 g |
| Sodium silicate No. 3 | 498 g |
| C solution: | |
| Water | 754 g |
| NaCl | 172 g |

A and B solutions were simultaneously added dropwise to C solution with vigorous stirring while maintaining the pH of the system at from 9 to 11 (several drops of a 48% aqueous NaOH solution were added to control the pH). The pH of the system at the time of completion of mixing was 9.5. The mixture was added to a 1-liter SUS autoclave, and hydrothermal synthesis was carried out at 160° C. for 20 hours with stirring (350 to 400 rpm). After cooling and filtration, the product obtained was thoroughly washed with a large amount of distilled water (about 7 liters) and filtered. After repeating this operation, the product was dried at 120° C. for 15 hours and calcined at 530° C. for 3 hours under air flow to obtain white powdery crystals. This product was identified to be ZSM-5 by X-ray diffraction measurement. Also, the $SiO_2:Al_2O_3$ molar ratio of this product was 64 by atomic absorption analysis.

Twenty grams of the Na-ZSM-5 thus obtained was subjected to ion exchange at 65° C. for 2 hours with 200 g of a 5% aqueous ammonium chloride solution and filtered, after which this operation was repeated three more times. The product was then washed with 200 g of distilled water and filtered, after which this operation was repeated four more times. The product was dried at 120° C. for 10 hours and calcined at 500° C. for 3 hours under air flow to obtain white powdery crystals.

EXAMPLE 1

To a 10-ml glass ampoule were added 0.6 g of ZSM-5 obtained in Reference example 1, 0.9 g of cyclohexene, 1.8 g of water and 0.9 g of phenol, and after sealing the ampoule, reaction was carried out at 100° C. for 8 hours. After cooling, the ampoule was opened, and the contents were taken out. n-Propanol was added to the contents to cause the oily and aqueous phases to mix homogeneously. Cyclohexanol in the resulting phase was quantitatively determined by gas chromatography to find that the yield of cyclohexanol was 41.9%.

EXAMPLE 2

Procedure was carried out in the same manner as in Example 1 except that salicylic acid was used in place of phenol, to find that the yield of cyclohexanol was 38.9%.

EXAMPLE 3

Procedure was carried out in the same manner as Example 1 except that 1-naphthol was used in place of phenol, to find that the yield of cyclohexanol was 32.6%.

EXAMPLE 4

To a 100-ml glass autoclave were added 5 g of ZSM-5 obtained in Reference example 1, 7.5 g of cyclohexene, 15 g of water and 7.5 g of phenol, and after closing the autoclave, reaction was carried out at 100° C. for 4 hours with stirring. After cooling and opening the autoclave, the oily phase was taken out (yield, 13.9 g) and cyclohexanol in it was quantitatively determined by gas chromatography to find that the cyclohexanol concentration was 19.8 wt. %. The cyclohexanol concentration of the aqueous phase was 1.6 wt. %. The yield of cyclohexanol, therefore, was 32.9%.

COMPARATIVE EXAMPLE 1

Procedure was carried out in the same manner as in Example 4 except that phenol was not added. As a result, the following were found: Weight of the oily phase, 8.2 g; cyclohexanol concentration of the oily phase, 8.0 wt. %; and cyclohexanol concentration of the aqueous phase, 1.9 wt. %. The yield of cyclohexanol, therefore, was 10.1%.

REFERENCE EXAMPLE 2

Stock solutions of the following compositions were first prepared.

| A solution: | |
|---|---|
| Water | 271 g |
| $H_2SO_4$ | 13.2 g |
| $Al_2(SO_4)_3 \cdot 16-18H_2O$ | 4.6 g |
| $(n-Pr)_4NBr$ | 19.9 g |
| NaCl | 46.9 g |
| B solution: | |
| Water | 198 g |
| Sodium silicate No. 3 | 159 g |

A and B solutions were mixed. The mixture was added to a 1-liter SUS autoclave, and hydrothermal synthesis was carried out at 120° C. for 72 hours and then at 160° C. for 5 hours with stirring (600 to 700 rpm). After cooling and filtration, the product obtained was thoroughly washed with a large amount of distilled water (about 3 liters) and filetered. After repeating this operation, the product was dried at 120° C. for 15 hours and calcined at 550° C. for 3 hours in an air atmosphere to obtain white powdery crystals. This product was identified to be ZSM-5 by X-ray diffraction measurement.

Ten grams of the Na-ZSM-5 obtained above was subjected to ion exchange at 60° C. for 1 hour with 100 g of a 5% aqueous ammonium chloride solution and filtered, after which this operation was repeated three more times. The product was then washed with distilled water, dried at 120° C. for 16 hours and calcined at 500° C. for 3 hours in an air atmosphere to obtain white powdery crystals.

EXAMPLE 5

To a 10-ml glass ampoule were added 0.6 g of ZSM-5 obtained in Reference example 2, 0.9 g of cyclohexene, 1.8 g of water and 0.3 g of 3-cresol, and after sealing the ampoule, reaction was carried out at 120° C. for 2 hours. After cooling, the ampoule was opened, and the contents were taken out. n-Propanol was added to the contents to cause the oily and aqueous phases to mix homogeneously. Cyclohexanol in the resulting phase was quantitatively determined by gas chromatography to find that the yield of cyclohexanol was 28.2%.

EXAMPLES 6 TO 13

Procedure was carried out in the same manner as in Example 5 except that phenols shown in Table 1 were used in place of 3-cresol. The results are shown in Table 1.

COMPARATIVE EXAMPLE 2

Procedure was carried out in the same manner as in Example 5 except that 3-cresol was not added, to find that the yield of cyclohexanol was 12.4%.

TABLE 1

|  | Phenols | Yield (%) |
|---|---|---|
| Example 5 | 3-Cresol | 28.2 |
| Example 6 | 4-Cresol | 27.9 |
| Example 7 | 2-Naphthol | 27.2 |
| Example 8 | 4-Chlorophenol | 31.5 |
| Example 9 | 4-Nitrophenol | 32.2 |
| Example 10 | 4-Cyanophenol | 30.0 |
| Example 11 | Salicylic acid | 28.8 |
| Example 12 | Hydroquinone | 18.7 |
| Example 13 | Pyrocatechol | 25.4 |
| Comparative example 2 | None | 12.4 |

EXAMPLE 14

Procedure was carried out in the same manner as in Example 1 except that ZSM-5 was replaced by JRC-Z-HM20 (reference catalyst of Nippon Shokubai Gakkai) and that reaction was carried out at 130° C., to find that the yield of cyclohexanol was 17.9%.

EXAMPLE 15

Procedure was carried out in the same manner as in Example 1 except that ZSM-5 was replaced by JRC-Z-HM15 (reference catalyst of Nippon Shokubai Gakkai) and that reaction was carried out at 130° C., to find that the yield of cyclohexanol was 15.8%.

EXAMPLE 16

To a 10-ml glass ampoule were added 0.9 g of cyclohexene, 1.65 g of water, 0.9 g of phenol and 1.35 g of Diaion RCP 147H, a sulfonic acid type cation exchange resin, (a product of Mitsubishi Chemical Industries, Ltd.). After sealing the ampoule, reaction was carried out at 120° C. for 8 hours. After cooling and opening the ampoule, the contents were taken out and separated into the reaction solution and resin. After washing the resin with n-propanol, the washing and reaction solution were combined and quantitatively determined for cyclohexanol by gas chromatography. As a result, the yield of cyclohexanol was 36.0%.

EXAMPLES 17 TO 24

Procedure was carried out in the same manner as in Example 16 except that phenols shown in Table 2 were used in place of phenol. The results are shown in Table 2.

COMPARATIVE EXAMPLE 3

Procedure was carried out in the same manner as in Example 16 except that phenol was not added, to find that the yield of cyclohexanol was 14.2%.

COMPARATIVE EXAMPLES 4 AND 5

Procedure was carried out in the same manner as in Example 16 except that compounds shown in Table 2 were used in place of phenol. The results are shown in Table 2.

TABLE 2

|  | Phenols | Yield (%) |
|---|---|---|
| Example 16 | Phenol | 36.0 |
| Example 17 | 1-Naphthol | 31.7 |
| Example 18 | Pyrocatechol | 31.4 |
| Example 19 | Salicylic acid | 30.7 |
| Example 20 | 2-Cresol | 28.5 |
| Example 21 | Hydroquinone | 25.0 |
| Example 22 | 2-tert-Butylphenol | 24.2 |
| Example 23 | 2-Chlorophenol | 22.9 |
| Example 24 | 2,6-Xylenol | 22.1 |
| Comparative example 3 | None | 14.2 |
| Comparative example 4 | 1,4-Dioxane | 13.7 |
| Comparative example 5 | Tetrahydrofurfuryl alcohol | 18.8 |

EXAMPLE 25

Procedure was carried out in the same manner as in Example 16 except that Amberlyst 15 (a product of Rohm & Haas Co.) was used in place of Diaion RCP 147H which is a sulfonic acid type ion exchange resin. As a result, the yield of cyclohexanol was 37.5%.

EXAMPLES 26 TO 35

Procedure was carried out in the same manner as in Example 25 except that phenols shown in Table 3 were used in place of phenol. The results are shown in Table 3.

COMPARATIVE EXAMPLE 6

Procedure was carried out in the same manner as in Example 25 except that phenol was not used, to find that the yield of cyclohexanol was 14.1%.

TABLE 3

|  | Phenols | Yield (%) |
|---|---|---|
| Example 25 | Phenol | 37.5 |
| Example 26 | 2-Isopropylphenol | 24.1 |
| Example 27 | 2-Ethylphenol | 25.4 |
| Example 28 | Sulfosalicylic acid | 14.3 |
| Example 29 | 4-Phenylphenol | 15.5 |
| Example 30 | 2-Naphthol | 33.1 |
| Example 31 | 2,3,5-Trimethylphenol | 25.1 |
| Example 32 | 4-Chlorophenol | 36.4 |
| Example 33 | 4-Nitrophenol | 34.1 |
| Example 34 | Pyrogallol | 22.2 |
| Example 35 | 4-Bromophenol | 27.3 |
| Comparative example 6 | None | 14.1 |

What is claimed is:
1. A method for producing a cycloalkanol having from 5 to 8 carbon atoms by the hydration of a cycloalkene having from 5 to 8 carbon atoms with water using a solid acid as a catalyst which comprises carrying out said hydration at a temperature in the range from about 50° C. to about 200° C. in the presence of a phenol having one or more hydroxyl groups directly bonded to a benzene ring.

2. A method according to claim 1, wherein the cycloalkene having from 5 to 8 carbon atoms is cyclopentene, cyclohexene, cyclooctene or 1,5-cyclooctadiene.

3. A method according to claim 1, wherein the cycloalkene and the cycloalkanol corresponding thereto are cyclohexene and cyclohexanol, respectively.

4. A method according to claim 1, wherein the phenol is one member selected from the group consisting of phenol, cresol, xylenol, trimethylphenol, ethylphenol, isopropylphenol, tert-butylphenol, phenylphenol, tolylphenol, cyanophenol, chlorophenol, bromophenol, iodophenol, pyrocatechol, resorcinol, hydroquinone, pyrogallol, hydroquinone monomethyl ether, methyl salicylate, salicylic acid, 4-hydroxybenzoic acid, nitrophenol, mercaptophenol, methylthiophenol, phenolsulfonic acid, naphthol, and sulfosalicylic acid.

5. A method according to claim 1, wherein the amount of the phenol used is from about 0.01 to about 10 moles based on 1 mole of the cycloalkene.

6. A method according to claim 1, wherein the solid acid as catalyst is mineral acid, metal salt, ion exchanger, or metal oxide.

7. A method according to claim 6, wherein the mineral acid is phosphoric acid, heteropoly-acid or their salt supported on carriers, or silicophosphoric acid.

8. A method according to claim 6, wherein the metal salt is the sulfate of Fe, Al, Cr, Co and Cu, the sulfate supported on silica, or the phosphate of B, Al, Cr, Zr, Fe and Mn.

9. A method according to claim 6, wherein the ion exchanger is sulfonic acid type cation-exchange resin, acid-treated or ion-exchanged montmorillonite.

10. A method according to claim 6, wherein the metal oxide is tungsten oxide, mixture of the tangsten oxide with ZnO or $Cr_2O_3$, $Al(OH)_3$, $SiO_2.Al_2O_3$, zirconium tungstate, $MoO_3$-$ZrO_2$, $TiO_2$-$SiO_2$, $TiO_2$-ZnO, $NbO_3.nH_2O$, or zeolite.

11. A method according to claim 1, wherein the amount of the water used is from about 1 to about 100 moles based on 1 mole of the cycloalkene.

* * * * *